(12) United States Patent
Nissels et al.

(10) Patent No.: US 8,540,781 B2
(45) Date of Patent: Sep. 24, 2013

(54) FOOT PROSTHESIS

(75) Inventors: Volker Nissels, Bayreuth (DE); Christof Kurth, Heinersreuth (DE); Werner Kranner, Bad Aibling (DE)

(73) Assignee: Medi GmbH & Co. KG, Bayreuth (DE)

( * ) Notice: Subject to any disclaimer, the term of this patent is extended or adjusted under 35 U.S.C. 154(b) by 76 days.

(21) Appl. No.: 13/210,803

(22) Filed: Aug. 16, 2011

(65) Prior Publication Data

US 2012/0046760 A1 Feb. 23, 2012

(30) Foreign Application Priority Data

Aug. 19, 2010 (DE) .......................... 10 2010 034 893

(51) Int. Cl.
*A61F 2/66* (2006.01)
(52) U.S. Cl.
USPC ............................................................ 623/55
(58) Field of Classification Search
USPC .................................................... 623/47–56
See application file for complete search history.

(56) References Cited

U.S. PATENT DOCUMENTS

| | | | | | |
|---|---|---|---|---|---|
| 2,197,093 | A | * | 4/1940 | Campbell | 623/56 |
| 4,547,913 | A | * | 10/1985 | Phillips | 623/27 |
| 4,892,553 | A | * | 1/1990 | Prahl | 623/55 |
| 5,112,356 | A | * | 5/1992 | Harris et al. | 623/49 |
| 6,029,374 | A | * | 2/2000 | Herr et al. | 36/27 |
| 6,197,068 | B1 | * | 3/2001 | Christensen | 623/55 |
| 6,261,324 | B1 | | 7/2001 | Merlette | |
| 6,767,370 | B1 | * | 7/2004 | Mosler et al. | 623/55 |
| 6,929,665 | B2 | * | 8/2005 | Christensen | 623/52 |
| 6,942,704 | B2 | | 9/2005 | Sulprizio | |
| 2005/0038524 | A1 | | 2/2005 | Jonsson | |
| 2005/0234563 | A1 | * | 10/2005 | Phillips | 623/55 |
| 2007/0213831 | A1 | | 9/2007 | De Cubber | |
| 2008/0033578 | A1 | | 2/2008 | Christensen | |
| 2009/0012630 | A1 | * | 1/2009 | Mosler et al. | 623/55 |
| 2009/0157197 | A1 | * | 6/2009 | Bonacini | 623/55 |
| 2009/0306792 | A1 | | 12/2009 | Lecomte et al. | |
| 2010/0042228 | A1 | | 2/2010 | Doddroe et al. | |
| 2012/0271434 | A1 | * | 10/2012 | Friesen et al. | 623/55 |

FOREIGN PATENT DOCUMENTS

| | | |
|---|---|---|
| DE | 40 37 928 A1 | 5/1992 |
| DE | 10 2006 004 132 A1 | 8/2007 |
| DE | 10 201 034 893.7 A1 | 2/2012 |
| JP | 2007502629 A | 2/2007 |
| RU | 2068248 C1 | 10/1996 |
| RU | 2291676 C2 | 1/2007 |
| WO | 0230340 A2 | 4/2002 |

\* cited by examiner

*Primary Examiner* — David Isabella
*Assistant Examiner* — Marcia Hoffman
(74) *Attorney, Agent, or Firm* — Lucas & Mercanti, LLP

(57) ABSTRACT

Foot prosthesis, comprising an upper part, and a lower part that is placed on the ground when walking, wherein the upper part and the lower part are connected to each other via an elastic damping element arranged in the heel area, and the upper part and the lower part, forming a spring, extend one above the other and spaced apart from each other into the area of the forefoot, wherein at least one filling piece (15) is inserted between the upper part (3) and the lower part (4) in the area between the damping element (9) and the forefoot (5), which filling piece (15) increases the flexural stiffness of the upper and lower part coupled via the filling piece during walking.

16 Claims, 5 Drawing Sheets

FOOT PROSTHESIS

Figure 1:
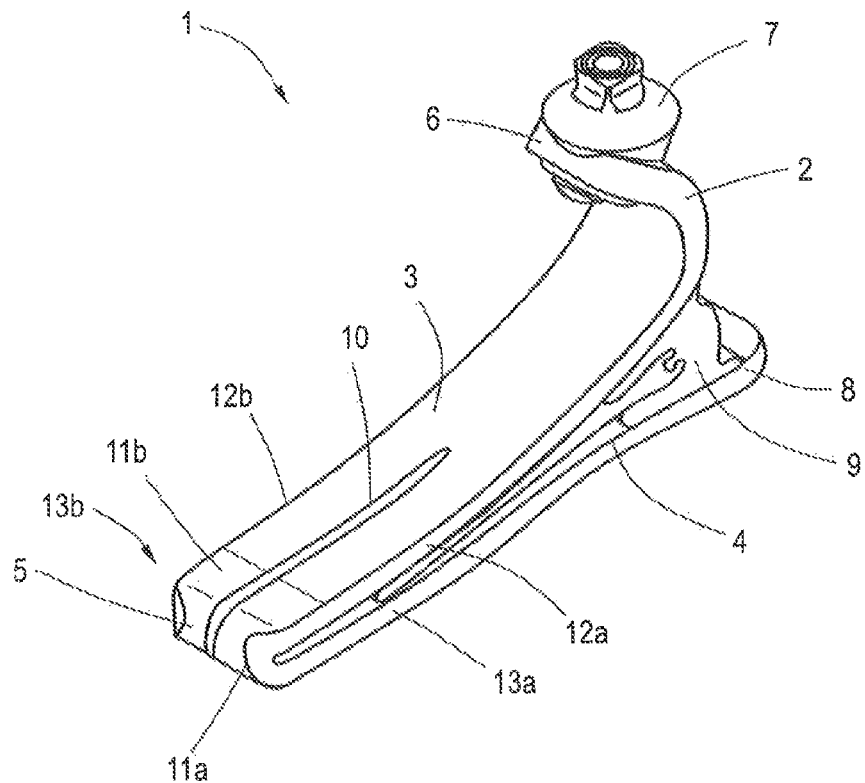

This application claims the priority of DE 10 2010 034 893.7-35 filed Aug. 19, 2010, which is incorporated by reference herein.

The invention relates to a foot prosthesis, comprising an upper part, and a lower part that is placed on the ground when walking, wherein the upper part and the lower part are connected to each other via an elastic damping element arranged in the heel area, and the upper part and the lower part extend one above the other and spaced apart from each other into the area of the forefoot.

A foot prosthesis of the kind described allows the wearer to set the foot down in a comfortable manner damped via the damping element and provides a walking pattern similar to the natural foot. Modern foot prostheses are composed, for example, of a carbon fiber laminate. They have an upper part, by which the foot prosthesis is coupled via a suitable connecting means to a connecting shaft or the like, with which the entire prosthesis is secured on the leg stump. The upper part has an approximately horizontally extending portion, which reaches from the heel area as far as the forefoot area. In the area of the forefoot, the upper part is connected to a lower part, which is placed on the ground during walking. Upper part and lower part are spaced apart from each other but lie approximately congruently one above the other. Located between them, in the heel area, there is an elastic damping element, for example made of a rubber-like material, which acts as impact damper and damps the force that arises on set-down. In the area between damping element and forefoot, the upper part and lower part form a spring, which is bent and stressed during walking. During a walking movement, the foot prosthesis is placed with the rear end of the lower part on the ground. The heel elastomer acts as impact damper and point of rotation between rear foot lever and front foot lever, that is to say between heel area and forefoot area. The rear foot lever is pretensioned upwardly by the ground reaction force, which results in a torque in the damping element. In this way, the front foot area, that is to say the area between damping element and forefoot, is pretensioned, such that this portion widens, that is to say the upper part moves away from the lower part in this area, resulting in an upward bending. In this way, energy is stored there. This energy is released again when the front foot makes ground contact, that is to say when the forefoot is also set down, and thus facilitates the forward movement. Upon transition into the early stance phase, the vector of the ground reaction force, which vector hitherto lay behind the damping element, that is to say in the rear heel area, migrates in front of the damping element. This results in a moment in the damping element as point of rotation, which moment presses together the lower area and the upper area of the front foot. That is to say, as a result of the shift in weight, the previous widening between upper part and lower part is reduced again. This moment becomes greater during the course of the roll-over, since the vector of the ground reaction force migrates even further forward, as a result of which the two areas of the upper part and of the lower part that were previously tensioned apart move even closer to each other, until they come into contact with each other, initially with linear contact and later with planar contact. Starting from this point in time when contact occurs, the front foot resistance rises over-proportionally. That is to say, much greater resistance is offered to any elastic foot deformation, resulting from the mutually contacting areas of the upper part and of the lower part in the area between damping element and forefoot.

In modern prostheses made of carbon material, the basic hardness of the foot prosthesis, that is to say its bendability in the area of the spring and its rollability, is fixed by the respective hardness of the upper part and lower part, i.e. by the actual material of the parts, in other words, depending on the desired hardness, the carbon material forming the prosthesis is accordingly made thicker or accordingly harder, etc. The orthopedic technician or the user is not provided with any possibility of adjusting the hardness.

Therefore, the problem addressed by the invention is that of making available a foot prosthesis offering the possibility of adjusting the hardness.

To solve this problem in a foot prosthesis of the kind mentioned in the introduction, provision is made, according to the invention, that at least one filling piece is inserted between the upper part and the lower part in the area between the damping element and the forefoot, which filling piece increases the flexural stiffness of the upper and lower part coupled via the filling element during walking.

The foot prosthesis according to the invention is characterized in that a filling piece is inserted into the area between damping element and forefoot, in other words into the hollow space formed there between upper part and lower part. During the walking movement, this filling piece comes into contact with one or both of the mutually facing surfaces of the upper part and lower part, depending on the design of the filling piece. This results in a change in the process of contacting or coupling of the upper part to the lower part which, according to the invention, are coupled via the filling piece. The movement of the upper part during walking and relative to the lower part is met with resistance by the filling piece, on which both temporarily bear, and this results in a stiffening of the spring formed by upper part and lower part in the area between damping element and forefoot. That is to say, a connection increasing the stiffness does not begin only during the walking movement when the upper part makes contact with the lower part, but much earlier than this, namely when a surface contact begins via the filling piece. Since the latter is arranged in the area between upper part and lower part, surface contact necessarily takes place much earlier in comparison to a foot prosthesis without an inserted filling piece. That is to say, a change in the flexural stiffness arises much earlier and, as a result, also at individually adjustable times. The contact also results in a change in the beginning displacement movement of the upper part relative to the lower part, which begins at the latest on lifting the foot or pressing down on the foot. Both parts move slightly relative to one another. This movement is met with resistance by the coupling via the filling element, which resistance likewise has a stiffening effect. The integration of the filling piece means that it is no longer necessary to have complete approximation of the upper part to the lower part, and instead an increase in resistance, and therefore a hardening of the prosthesis, already takes place when the upper part has come close enough to the lower part that contact is made with the filling piece and, consequently, because of the surface contact, a compression, possible only against increased resistance, and relative displacement of upper part to lower part is possible.

That is to say, with the filling piece integrated according to the invention between the upper area and lower area of the front foot, that is to say the upper part and lower part, there is the possibility of individually adjusting the phase of the step cycle starting from which the front foot hardness begins to increase overproportionally. This therefore gives the orthopedic technician the possibility to individually adapt the foot prosthesis such that it is as comfortable as possible for the wearer, in which case, of course, the individual adaptation also can be made depending on the respective use situation (foot prosthesis for leisure use, foot prosthesis for sport).

The filling piece itself is preferably a planar component with at least one adhesive contact surface and can be fitted in different ways between upper part and lower part.

According to a first alternative of the invention, the filling piece can be fixedly connected, for example glued, to the upper part or the lower part. According to this alternative, the filling piece is securely fixed by the orthopedic technician according to the individual, wearer-specific choice and, if appropriate, adaptation. During walking, it comes into contact with the respectively opposite part, thus generating the resistance. Therefore, if the filling piece is, for example, an elongate planar plastic component made of a sufficiently elastic elastomer, it is glued, for example, to the lower part and, during walking, comes into contact with the upper part. The fact that the filling piece is fitted by the orthopedic technician means that the prosthesis and the spring behavior thereof can be precisely adapted and adjusted to the individual requirements of the wearer.

In one alternative, the filling piece is arranged releasably on the upper part, on the lower part or on the damping element. This possible alternative to fixed gluing offers the orthopedic technician or wearer the particular advantage of removing the filling piece when necessary or replacing it with another filling piece. This therefore gives a very high degree of flexibility with respect to the individual damping or hardness of the foot prosthesis design, since the orthopedic technician or wearer can vary the prosthesis set-up as and when desired, by removing a filling piece or replacing it with another softer or harder or longer or shorter filling piece. The basic selection and individual adaptation of the filling piece and therefore the adjustment of the prosthesis are done by the orthopedic technician, while the advantages of replaceability are also afforded to the wearer.

In an expedient development of this alternative of the invention with releasable filling piece, a first securing portion is provided on the damping element, and a second securing portion complementing the first securing portion is provided on the filling piece, and these securing portions can be brought into releasable engagement with each other. According to this embodiment, the filling piece is therefore preferably secured on the damping element. For this purpose, two securing portions of complementary design are provided, one on the damping element and one on the filling piece, which securing portions are to be brought into releasable engagement with each other for fixing.

Secure fixing is achieved, for example, by virtue of the fact that the first securing portion is a groove, which is open toward the forefoot and has an undercut and elongate holding projection in the inside, and the second securing portion is a holding claw, which is shaped to complement the groove and the holding projection and engages around the holding projection. The groove provided on the damping element can easily be made deep enough, since the damping element itself has a certain horizontal length. A secure and form-fit retaining connection is achieved by means of the complementary shape of the groove with holding projection, designed for example as a projecting bead with circular cross section, and of the holding claw.

Since there is relatively little room between upper part and lower part, with the spacing in this area ranging for example between 0.5 cm and 2 cm, an expedient development of the invention is one in which the filling piece can be pushed with its second securing portion sideways into the first securing portion. That is to say, the filling piece is to be pushed in sideways and thus brought between upper part and lower part. In order to prevent the filling piece from slipping out laterally, a development of the invention is proposed in which locking elements, for example a groove and a projection and the like, can be provided on the first and second securing portions and cooperate in the insertion position. In this way, the filling piece is fixed securely in its lateral orientation.

In an alternative to the above-described design of the two securing portions as structures of complementary shape engaging in each other, a variant of the invention is proposed in which a first securing portion is provided on the damping element and a second securing portion is provided on the filling piece, said securing portions being designed as apertures which, in the insertion position, provide a passage for a holding pin, preferably introduced from the direction of the upper part, or a holding screw, which is likewise preferably introduced from the direction of the upper part and which engages in an internally threaded portion optionally provided on the damping element. For example, the damping element can once again be provided with a groove, which in this case however is not undercut or otherwise shaped but instead has a simple rectangular structure or one open toward the front. An aperture, that is to say a bore, is formed from the top. A complementary bore that is to be positioned congruently is located on the filling piece, which for example is once again pushed in from the side. When the bores lie congruently, a holding pin can be passed from above through the upper part and fixes the filling piece in the damping element. It is also conceivable, for this purpose, to use a screw and, for example, to insert a sleeve with an internal thread into the damping element, into which thread the screw is screwed. In this way too, the filling piece can be safely secured and easily released by the wearer. The deformability of the upper part must not be impaired by the holding element used, e.g. the screw. Therefore, this screw serves only for the connection of damping element and filling piece, it is not therefore mounted on the upper part.

Although it is already sufficient and advantageous to provide a securing portion on the filling piece only at one longitudinal end, it is of course also conceivable to design the filling piece with a securing portion at both longitudinal ends, such that the filling piece can also be used when turned through 180°. This is especially advantageous when, as will be discussed in detail below, the filling piece is made of different hard materials or has portions of different Shore hardness, etc.

In an expedient development of the invention, the upper part and the lower part are longitudinally slit from the direction of the forefoot so as to form two adjacent longitudinal portions. This longitudinal slit thus permits the formation of two adjacent springs which, during walking, are loaded differently on account of the pronation or supination movement of the wearer. If the filling piece extends into the slit area, in other words if it lies in such a longitudinal portion, this means that the respective pronation or supination movement can also be changed or adjusted by the action of the filling piece.

The width of the filling piece itself corresponds substantially to the width of the upper part and lower part, although the filling piece can also have at least in some areas a smaller width than the upper part and lower part.

If the foot prosthesis is slit longitudinally, in other words if springs are formed by two adjacent longitudinal portions, a particularly advantageous development of the invention is one in which the filling piece, at least in the area with which it is arranged between two mutually superposed longitudinal portions of the slotted upper part and lower part, has only the width of the longitudinal portions. That is to say, the filling piece is so dimensioned that it extends only in the area of the right-hand or left-hand spring, that is to say of the right-hand or left-hand longitudinal portion pairing, and, consequently, only this area is influenced by the action of the filling piece. As a result, this provides locally and individually the possibility, depending on the nature of the natural movement, of influencing the right-hand spring or left-hand spring and therefore the respective pronation or supination movement via the filling piece. A further advantage also lies in the fact that, in connection with the longitudinal slit and the possibility of individual "side" influence, the foot prosthesis according to the invention can be worn both on the right leg and also on the left leg. Through the possibility of integration of a filling piece that acts only partially or in some areas as seen as it were in the lateral direction, the hardness can be adjusted in such a way that it is accordingly adjusted specifically to the situation that arises when the prosthesis is worn on the left or right leg. That is to say, the behavior in terms of hardness or stiffness or damping in the medial-lateral or internal-external direction can be adjusted via the filling piece. During the walking movement, the load line therefore "migrates" as it were from one side to the other side, as a result of the only local action of the filling piece.

To further improve the variability of the foot prosthesis according to the invention, the filling piece can be made of several materials with different Shore hardnesses or, if made from one material, can have areas with different Shore hardnesses. It is therefore possible to give the filling piece locally different hardnesses or elasticities, either by using different types of materials, which have different Shore hardnesses, or by using only one material, which is however made locally different. Of course, exchangeable filling pieces with different Shore hardnesses can also be made available.

The portions made of different materials or the areas of different Shore hardness can be arranged alongside each other in the transverse direction or in the longitudinal direction. That is to say that areas of different hardness lie one behind the other in the longitudinal direction, although they can also equally vary in the transverse direction. Depending on the design, the hardness of the front foot area again varies correspondingly.

Alternatively or in addition to the use of materials of different hardness or to the design of areas of different hardness, it is possible that the filling piece also has a thickness varying over its length and/or width. That is to say, for example, it can be thicker laterally than medially, or vice versa, and thickened areas, e.g. wave-shaped thickened areas, can also be formed in succession in the longitudinal direction. By means of such variations in thickness, the local contact areas can vary as it were as a function of the load or of the progress of the step movement. For example, if the waves arranged in succession in the longitudinal direction are provided, the wave peaks first come into contact with the respective surface of the upper part and lower part during the set-down movement or roll-over movement. As the movement progresses further, the wave peaks are increasingly compressed, the contact surfaces become larger, and the resistance increases still further.

The filling piece itself can be formed as a solid material component made of an elastic material. However, it is also conceivable to use a foamed elastic plastic, that is to say the filling piece is a foamed plastic component. However, it is also conceivable to use an incompressible filling piece.

It is possible to use any plastic that has the desired elasticity or Shore hardness and that also has a sufficient coefficient of friction or adhesiveness, so as to ensure that the resistance is increased. This is because the increase in resistance is after all also associated with the adhesiveness of the filling piece to the respective surface of the upper part and lower part.

The upper part and the lower part themselves are preferably formed integrally with each other. If the foot prosthesis is a carbon fiber laminate component, then only one carbon fiber element is used that extends as it were in a loop shape and as integral component forms the lower part, which merges in the forefoot area into the upper part. As an alternative to this, it is also conceivable that the upper part and the lower part are connected to each other in the area of the forefoot by a connecting means. It is conceivable, for example, to fix both parts to each other with a screw connection, and, if the prosthesis is designed as a longitudinally slit component, each spring has its own separate connecting means between upper part and lower part.

As has been described, it is possible for the wearer to adjust the hardness of the foot prosthesis as desired. If the filling piece is a component made of an elastic plastic, it is readily possible to individually establish the desired shape of the filling piece by suitable cutting to size of the filling piece. That is to say, the orthopedic technician or the actual wearer can define the desired and, if appropriate, also asymmetrical geometry of the filling piece. It is also possible to vary the length of the filling piece, in which case length markings are expediently provided on at least one side of the filling piece, which markings provide the wearer with relevant information as to how far, for example, the filling piece extends into the front foot area, etc. In this way too, the filling piece can be suitably adapted to foot prostheses of different lengths.

Figure 2:
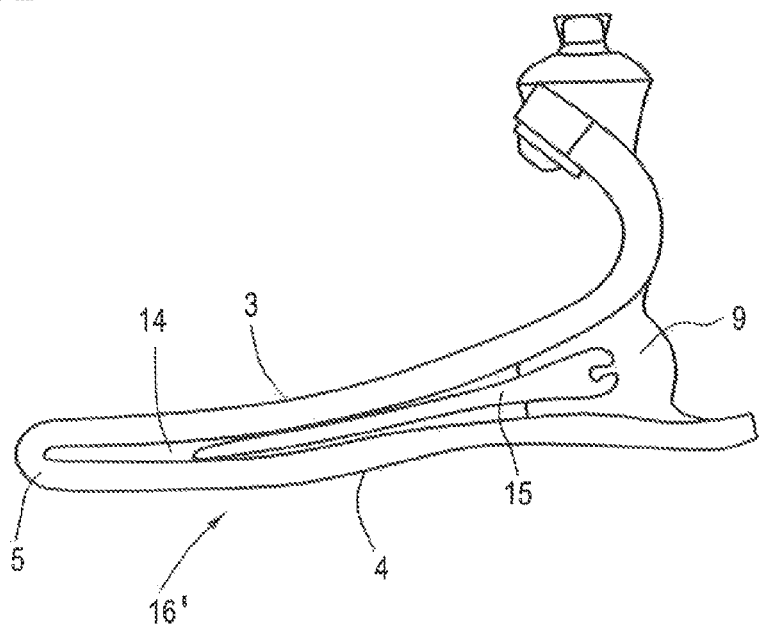
Figure 3:
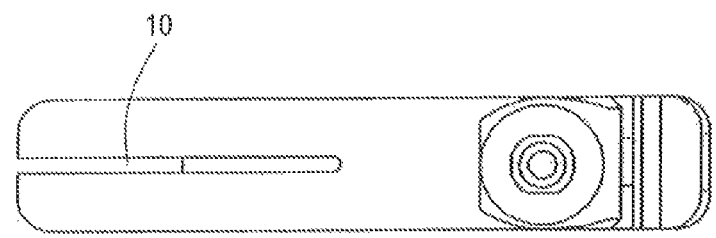
Figure 4:
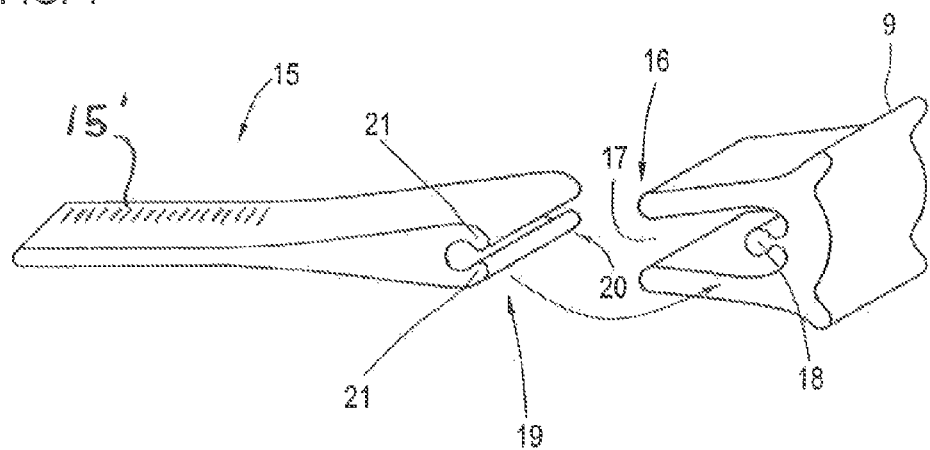
Figure 5:
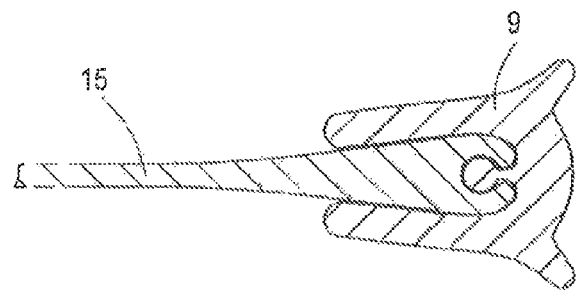
Figure 6:
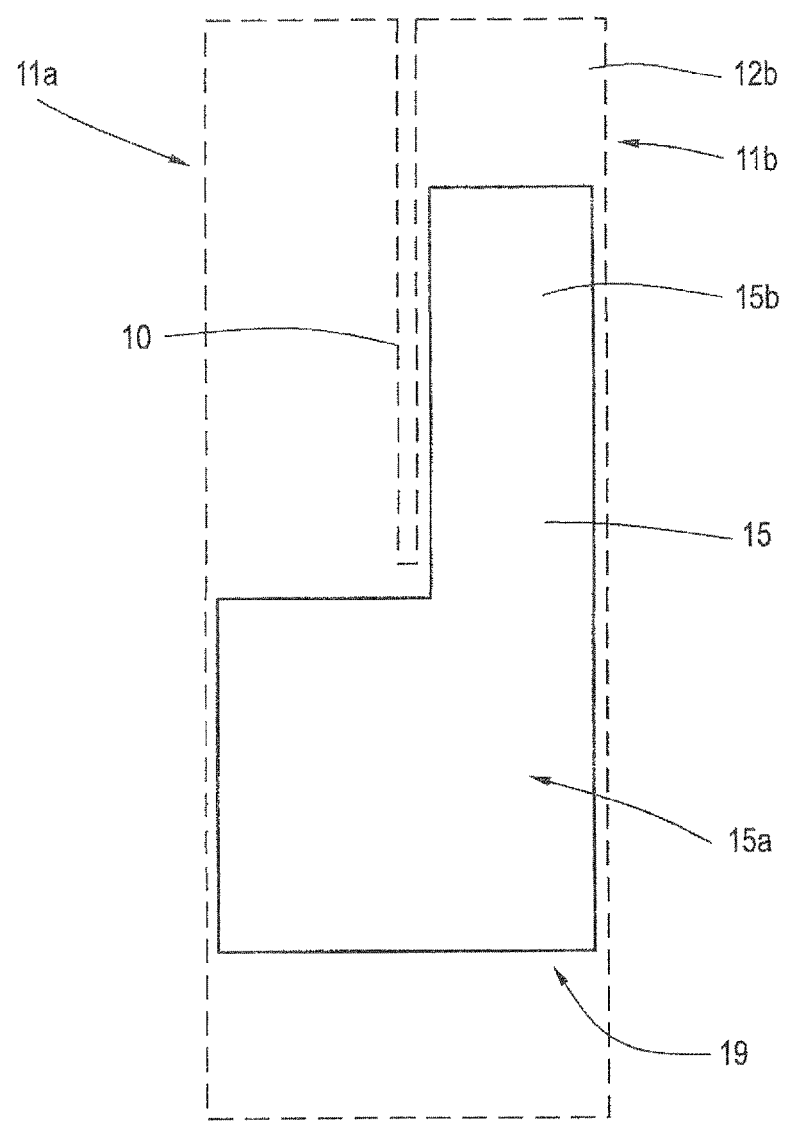
Figure 7:
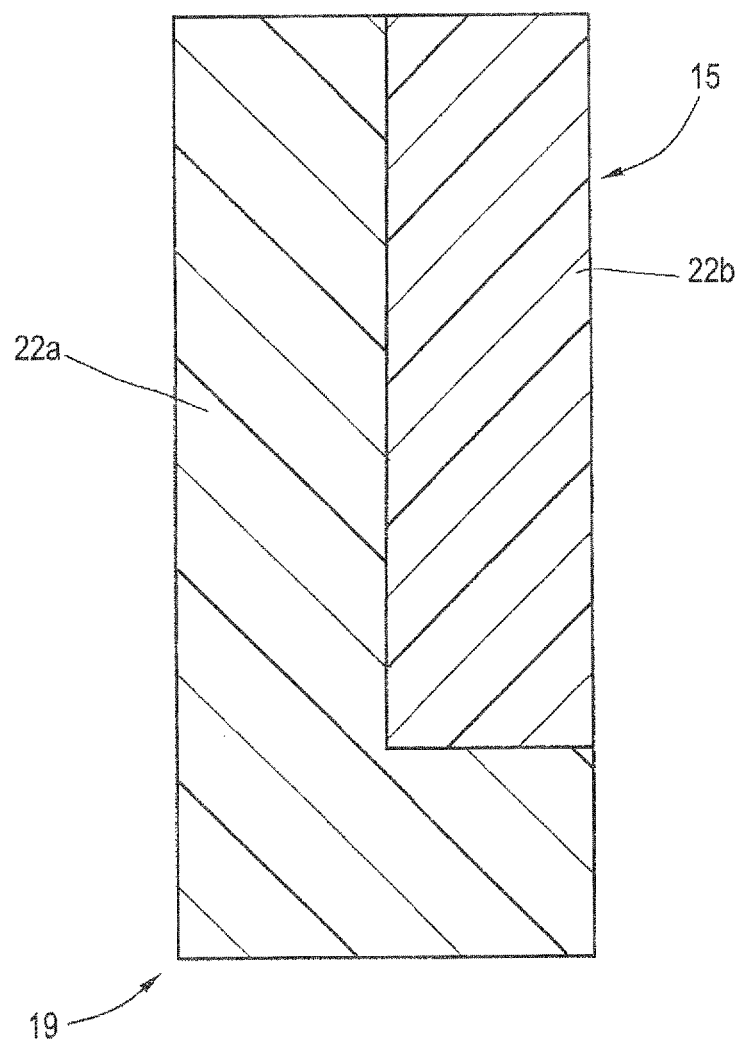
Figure 8:
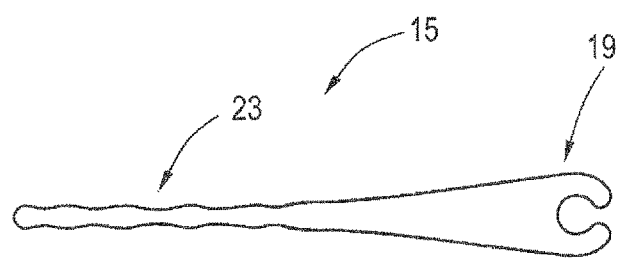
Figure 9:
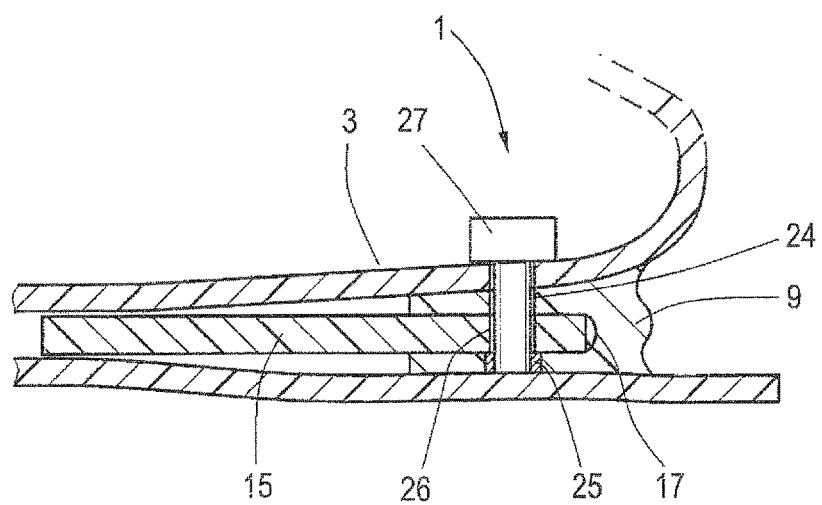

Further advantages, features and details of the invention will become clear from the illustrative embodiments described below with reference to the drawing, in which:

FIG. 1 shows a perspective view of a foot prosthesis according to the invention, FIG. 2 shows a side view of the foot prosthesis from FIG. 1, FIG. 3 shows a plan view of the foot prosthesis from FIG. 1, FIG. 4 shows a detail view of the damping element and of the filling piece when separate, FIG. 5 shows an enlarged sectional view of the area of connection of the damping element to the filling piece, FIG. 6 shows a view of a second embodiment of the filling piece, FIG. 7 shows a view of a third embodiment of the filling piece, FIG. 8 shows a side view of a fourth embodiment of the filling piece, and FIG. 9 shows a schematic diagram of a second way of securing the filling piece to the damping element.

FIG. 1 shows a foot prosthesis 1 according to the invention, consisting of a one-piece carbon fiber laminate component 2, which has an upper part 3 and, guided underneath the upper part 3, a lower part 4, said upper part 3 and lower part 4 being connected integrally to each other in the area of the forefoot 5. At the upper end 6 toward which the upper part 3 curves, there is an attachment means 7 for connecting the foot prosthesis to a prosthesis holder. The lower part 4 itself is placed on the ground during walking, and the rear end 8 forms the heel part.

In the area of the rear end 8, that is to say in the heel area, the upper part 3 and the lower part 4 are connected to each other via a damping element 9. This damping element 9 is made of an elastic material, primarily a rubber or plastic component, which is connected fixedly, preferably glued, to the upper part 3 and lower part 4.

The upper part 3 and the lower part 4 (see FIGS. 1 and 3) are separated along part of their length by a longitudinal slit 10, such that two separate springs 11a, 11b are formed, each one consisting of two longitudinal portions of the upper part 3 and lower part 4, namely the longitudinal portions 12a, 12b of the upper part 3 and the longitudinal portions 13a, 13b of the lower part 4. That is to say, the two springs 11a, 11b are movable separately from each other and can be compressed separately from each other.

As can be seen in particular from FIG. 2, a hollow space 14 is formed between upper part 3 and lower part 4, into which hollow space 14, in the foot prosthesis according to the invention, a filling piece 15 is inserted. This filling piece 15 is designed as a planar, elongate and tongue-like component. With one end it is secured to the damping element 9, as will be discussed in more detail below. It extends, for example, along approximately ⅔ of the length of the hollow space from the damping element 9 to the forefoot 5. Its width is dimensioned so as to correspond substantially to the width of the upper part 3 and lower part 4, which are both the same width.

Its function is such that, during a walking movement starting with the set-down of the heel area 8 of the lower part 4 and up to the end of the step when the wearer places weight on the forefoot 5, it frictionally couples the upper part 3 to the lower part 4 temporarily after a defined walking phase is reached, such that the upper part 3 and lower part 4 are connected to each other via the filling piece 15. During the walking movement, a relative movement of upper part 3 to lower part 4 takes place which, because of the weight load of the foot prosthesis 1, starts as a result of the weight of the wearer, particularly when the area of the front foot 16' is set down and the wearer begins the roll-over to the forefoot 5 and places weight on the latter. In this process, the upper part 3 and lower part 4, which are initially tensioned apart from each other when the heel area 8 is set down because of the elasticity of the prosthesis material, move back toward each other, that is to say the height of the hollow space 14 decreases. Starting from a defined time, the inner surfaces of the upper part 3 and lower part 4 bear on the filling piece 15 which, because of the choice of its material, has a sufficient coefficient of friction and offers good adherence to the respective bearing surface. As the movement continues, the upper part 3 and lower part 4 can no longer move undamped relative to each other, both as regards the movement toward each other and also as regards the longitudinal shift relative to each other, which longitudinal shift is relatively slight. Instead, the movement is damped via the filling piece 15, that is to say an increased resistance is offered to this movement via the filling piece 15 as a result of the surface coupling. This has the result that in particular the area of the front foot 16', that is to say the spring, becomes harder overall, thus no longer being so easily deformable, since the bending movement in this area is resisted by the filling piece 15 and the surface coupling. Consequently, during walking, the foot prosthesis 1 is no longer "soft" or elastic compared to the prosthesis without inserted filling piece 15.

The filling piece 15 is secured releasably to the damping element 9, that is to say can be inserted and removed as and when desired by the wearer. For this purpose, a first securing portion 16 is provided on the damping element 9, said securing portion 16 consisting of a groove 17, in the rear end of which is formed an elongate holding projection 18 of circular cross section undercut on both sides.

A second securing portion 19 is formed at the rear end of the filling piece 15 and has a shape complementing the groove 17 and the holding projection 18. It has a groove 20 which complements the shape of the holding projection 18 and which on both sides has claw-like portions 21, of which the shape again corresponds to the groove shape around the holding projection 18. That is to say, the second securing portion is designed as a holding claw.

For assembly, the filling piece 15 is pushed from the side into the groove 17 in the damping element 9. As is shown in the enlarged sectional view according to FIG. 5, the two holding portions 16, 19 engage in each other with a form fit in the assembly position. The arrangement of the holding projection 18 on the damping element 9 and of the holding claw on the filling piece 15 ensures that, when the heel is set down, i.e. when the force is introduced behind the damping element 9, the latter does not open and the connection come loose. If the front area of the groove 17 opens slightly at all, the area of the claw-like engagement does not, and this means that secure fixing is provided at all times independently of the respective walking phase.

FIG. 6 shows a schematic diagram of another embodiment of a filling piece 15. This one is asymmetrical. With its rear end, on which the second securing portion 19 (not shown) is provided, it is once again fixed in the damping element 9 (not shown here), in the same way as in FIG. 4. It extends with its wide area 15a into the area of the front foot 16, in which area the upper part 3 and lower part 4 already lie one above the other. The wide area 15a corresponds substantially to the width of the upper part 3 and lower part 4. This portion extends substantially as far as the end of the longitudinal slit 10 of the carbon fiber laminate component 2, indicated here only by broken lines. The portion 15a is adjoined by an extended portion 15b, which is much narrower however, its width corresponding substantially to the width of the two longitudinal portions 12b, 13b lying one above the other, that is to say of the spring 11b, in relation to the view in FIG. 1. That is to say, the filling piece 15 here influences the bending behavior in the area of the right-hand spring 11b, and the latter, because of the coupling of the longitudinal portions 12b, 13b via the filling piece 15 and the portion 15b, becomes harder compared to the spring 11a between which no portion of the filling piece 15 engages. This spring 11a is therefore softer compared to the spring 11b. This now has the effect that, depending on the walking style, the pronation or supination can be influenced, in the context of which the springs 11a, 11b are asymmetrically loaded on account of a rotation of the foot. Of course, it is possible that the filling piece 15 is also differently designed and the extended portion 15b is arranged on the other side, such that this portion 15b extends into the area of the spring 11a, which is then influenced, while the spring 11b is uninfluenced. Consequently, the load characteristic with respect to the longitudinal axis of the foot can be varied, either by a filling piece 15 being introduced between both springs 11a, 11b or only in the area of one spring. This can be adjusted as desired by the wearer, depending on what is found to be more comfortable.

FIG. 7 shows another embodiment of a filling piece 15 which, in respect of its second securing portion 19, is again designed as shown in FIG. 4. It has a uniform width along its length, but it has two portions 22a, 22b of different hardness, as is indicated by the different hatching. For example, the portion 22b is harder than the portion 22a, that is to say the material there has a higher Shore hardness than in the other portion. This can be achieved, for example, if the portions 22a, 22b are made of different plastics, which can easily be injected jointly in a common manufacturing method. However, it is also conceivable to use the same plastic for both portions, but to slightly adjust the local Shore hardness thereof by suitable additives. In each case, by means of such an element, the elasticity behavior of one spring 11a, 11b can again be adjusted so as to be different than that of the other spring. The width of the portion 22b corresponds substantially to the width of one spring 11a, 11b (in the example shown this would be the spring 11b), while the width of the adjacent narrow area of the portion 22a corresponds to the width of the spring 11a. The spring 11b would therefore be assumed to be harder than the spring 11a.

Since the second securing portion 19 has a symmetrical structure, it is possible for the filling piece 15 to be used also when turned through 180°. That is to say, the wearer can position the portion 22b, which is assumed to be somewhat harder in the example, in the spring 11a, while the softer portion 22a would be positioned in the spring 11b.

Although this is not shown, the portions 22a, 22b can also be separated from each other by a longitudinal slit, in which case the longitudinal slit would then extend congruently with respect to the longitudinal slit 10 of the prosthesis.

In addition, and this applies to all of the described embodiments, the possibility of the filling piece 15 being made of an elastic material gives the orthopedic technician or the wearer the possibility of cutting the filling piece to size when necessary, with scissors or the like. For example, a filling piece 15 homogenous in nature, as shown in FIG. 4, can be easily cut to a shape as shown for the filling piece 15 in FIG. 6. It is also possible for the filling piece 15 from FIG. 7 to be partially cut to size in such a way that one or other area 22a, 22b is cut out, if this appears more comfortable. Also, filling piece 15 can have length markings 15' on at least one side as shown in FIG. 4.

FIG. 8 shows a side view of another embodiment of a filling piece 15, which again has the second securing portion 19, but, instead of a planar shape, it has an undulating profile 23. This has the effect that the wave peaks first come into contact with the surfaces of the upper part 3 and lower part 4. As the upper part 3 comes closer to the lower part 4, the wave peaks are compressed, the contact surface becomes larger, and the resistance offered as a result of friction increases overproportionally. In this way too, a variation in the prosthesis hardness can be achieved. Instead of an undulating profile, it would also be conceivable, for example, to have a zigzag profile.

Finally, FIG. 9 shows another embodiment of a foot prosthesis 1 in a partial view in which the filling piece 15 is secured in a different way than that described above. A substantially vertical bore 24 is provided on the damping element 9, and a threaded sleeve 25 is inserted into the bore 24, for example at the lower end thereof. At its rear end with which it engages in the groove 17 also provided here but without special contouring, the filling piece 15 likewise has a bore 26 which, in the assembly position, is flush with the bore 24 in the damping element 9. A fastening screw 27 is inserted from above, that is to say from the direction of the upper part 3, and is screwed into the threaded sleeve 25. The screw head rests on the damping element 9, and the upper part 3 is not connected to the screw. This again ensures secure fixing of the filling piece 15. Lateral fixing is at the same time provided by this screw 27. In the securing procedure described in relation to FIG. 4 et seq., lateral fixing can be achieved by the fact that, in the area of the interacting first and second securing portions 16, 19, locking portions that interact with each other in the correct assembly position, for example a narrow groove or depression and a correspondingly shaped projection, interact and thus provide lateral fixing.

Although a one-piece prosthesis component 2 is described in the figures, it is of course possible for upper part 3 and lower part 4 to be produced as separate components. These would then be connected to each other in the area of the forefoot 5 by a connecting element, for example by a screw connection or the like. The possibility of using a filling piece 15 applies equally in this embodiment. If a longitudinal slit for forming two separate and adjacent springs is also provided in this embodiment, both spring ends would have to be connected in the area of the forefoot 5 by corresponding connecting means.

The invention claimed is:

1. A foot prosthesis, comprising:
an upper part,
a lower part that is placed on the ground when walking,
an elastic damping element connecting the upper part and the lower part, the elastic damping element arranged in a heel area,
the upper part is connected to the lower part in a forefoot area so as to form a spring,
the upper part extending above the lower part and spaced apart from each other,
at least one filling piece positioned between the upper part and the lower part and positioned between the damping element and the forefoot area,
the filling piece increasing flexural stiffness of the upper part and the lower part during walking,
a first securing portion on the damping element between the upper part and the lower part,
a second securing portion on the filling piece at a heel end of the filling piece, the second securing portion releasably engaging the first securing portion so as to releasably engage the filling piece between the upper part and the lower part.

2. The foot prosthesis according to claim 1, wherein the filling piece is a planar component with at least one adhesive contact surface.

3. The foot prosthesis according to claim 1, wherein
the first securing portion is a groove, which is open toward the forefoot area and has an undercut and elongate holding projection inside the groove, and
the second securing portion is a holding claw, which is shaped to complement the groove and the holding projection and engages around the holding projection.

4. The foot prosthesis according to claim 3, wherein the second securing portion can be pushed sideways into engagement with the first securing portion.

5. The foot prosthesis according to claim 3, wherein locking elements are provided on the first and second securing portions which locking portions cooperate in the insertion position and prevent lateral slipping.

6. The foot prosthesis according to claim 1, wherein the upper part and the lower part are longitudinally slit in the forefoot area so as to form two adjacent longitudinal portions.

7. The foot prosthesis according to claim 6, wherein the filling piece has an area in the forefoot area, which is arranged between two mutually superposed longitudinal portions of the upper part and lower part, and the area of the filling piece has a width that is substantially a width of the two mutually superposed longitudinal portions.

8. The foot prosthesis according to claim 1, wherein
the filling piece has a width that corresponds substantially to a width of the upper part and lower part, or
the filling piece has at least in some areas a smaller width than the width of the upper part and lower part.

9. The foot prosthesis according to claim 1, wherein filling pieces with different Shore hardnesses can be used.

10. The foot prosthesis according to claim 1, wherein the filling piece is made of several materials having different Shore hardnesses or has several areas having different Shore hardnesses.

11. The foot prosthesis according to claim 10, wherein the portions made of different materials or the areas of different Shore hardness are arranged alongside each other in the transverse direction or in the longitudinal direction.

12. The foot prosthesis according to claim 1, wherein the filling piece has a thickness varying over its length and/or width.

13. The foot prosthesis according to claim 1, wherein the filling piece is formed as a solid material component made of an elastic plastic, or is formed as a foamed material component made of a foamed elastic plastic.

14. The foot prosthesis according to claim 1 wherein the upper part and the lower part are formed integrally with each other.

15. The foot prosthesis according to claim 1, wherein the upper part is connected to the lower part in the forefoot area by a connecting means.

16. The foot prosthesis according to claim 1, wherein length markings are provided on at least one side of the filling piece.

\* \* \* \* \*